United States Patent [19]

Bonivert et al.

[11] Patent Number: 4,812,210
[45] Date of Patent: Mar. 14, 1989

[54] MEASURING SURFACTANT CONCENTRATION IN PLATING SOLUTIONS

[75] Inventors: William D. Bonivert; Joseph C. Farmer, both of Livermore; John T. Hachman, Stockton, all of Calif.

[73] Assignee: The United States Department of Energy, Washington, D.C.

[21] Appl. No.: 109,008

[22] Filed: Oct. 16, 1987

[51] Int. Cl.$^4$ ............................................. G01N 27/46
[52] U.S. Cl. ..................................... 204/1 T; 204/434
[58] Field of Search ........................ 204/1 T, 434, 400

[56] References Cited

U.S. PATENT DOCUMENTS

| | | | |
|---|---|---|---|
| 4,132,605 | 1/1979 | Tench et al. | 204/434 |
| 4,146,437 | 3/1979 | O'Keefe | 204/434 |
| 4,246,343 | 1/1981 | Wilkins et al. | 435/32 |
| 4,443,301 | 4/1984 | Kerby | 204/1 T |
| 4,479,852 | 10/1984 | Bindra et al. | 204/434 |
| 4,503,383 | 3/1985 | Agar et al. | 324/61 P |
| 4,541,902 | 9/1985 | Kinoshita et al. | 204/1 T |
| 4,581,121 | 4/1986 | Dailey et al. | 204/406 |
| 4,589,958 | 5/1986 | Alexander et al. | 204/1 T |
| 4,631,116 | 12/1986 | Ludwig | 204/434 |
| 4,707,378 | 11/1987 | McBride | 204/434 |

OTHER PUBLICATIONS

Joseph Farmer, "Underpotential Deposition of Copper on Gold and the Effects of Thiourea Studied by AC Impedance", *Sandia Report Sand* 85-8626, 4/85.
*Journal of Electrochemical Science and Technology,* vol. 132, No. 11, Nov. 1985, pp. 2640-2648.

*Primary Examiner*—Ta-Hsung Tung
*Attorney, Agent, or Firm*—George H. Libman; James H. Chafin; Judson R. Hightower

[57] ABSTRACT

An arrangement for measuring the concentration of surfactants in a electrolyte containing metal ions includes applying a DC bias voltage and a modulated voltage to a counter electrode. The phase angle between the modulated voltage and the current response to the modulated voltage at a working electrode is correlated to the surfactant concentration.

12 Claims, 2 Drawing Sheets

MEASURING SURFACTANT CONCENTRATION IN PLATING SOLUTIONS

The U. S. Government has rights in this invention under contract DE-AC04-76DP00789 between the U. S. Department of Energy and AT&T Technologies, Inc.

BACKGROUND

The invention relates to measurement of surfactant concentration in an electrolytic solution and particularly to measurement of dilute organic additives in electroplating baths.

Surfactants are a class of materials which adsorb (stick) to the surface of a host material. It is often desirable to know the amount of a particular surfactant that is present in a liquid. For example, the concentration of surfactants is an important factor in electroplating. Electroplating involves the transfer of metal from an electrically conductive liquid (electrolyte) to a host metal.

In some cases, surfactants comprising various organic compounds are added to electroplating electrolytes to control the surface finish and mechanical properties of the resulting product. Since these additives may be consumed in the course of the electroplating process, it is desirable to monitor and adjust the additive concentration. In other cases, it is necessary to monitor the electrolyte to ensure that it contains no organic additives which under some conditions cause defects in the plating process.

U.S. Pat. No. 4,132,605 (Tench, et al.), discloses cyclic voltammetry and precisely controlled hydrodynamics to measure bulk metal deposition rates on a rotating disk working electrode. The deposition rate is correlated to additive concentration. The rotating working electrode, however, may be inconvenient in flow-through and handheld applications.

Each cycle in Tench requires more than one minute and generates a single data point; several data points are needed to reduce uncertainty in the measurement. There are many applications, however, in which greater speed and precision is desirable.

It is therefore an object of the invention to provide a fast and accurate measurement of surfactant concentration utilizing a stationery working electrode suited to hand-held wands and flow-through cells.

SUMMARY OF THE INVENTION

The invention is directed to an arrangement for measuring the concentration of a surfactant in an electrolytic liquid containing metal ions. A working electrode, a counter electrode, and a reference electrode are disposed in proximity and immersed in the liquid. A DC bias voltage and a modulated voltage are applied to the counter electrode. The magnitude of the DC bias voltage is selected to induce underpotential deposition of the metal ions on the working electrode. The difference in phase between the modulated voltage applied to the counter electrode and the response current at the working electrode is measured and correlated to provide a real-time indication of the surfactant concentration. The modulation frequency is selected at or near the high-frequency resonance for the working electrode. The voltage of the reference electrode controls a voltage follower. The output of the voltage follower regulates the current between the counter electrode and working electrode whereby underdeposition on the working electrode is sustained. Periodically, if necessary, the DC bias voltage applied to the counter electrode may be stepped (to a higher voltage) which cleanses the working electrode of any adsorbed surfactants.

BRIEF DESCRIPTION OF THE DRAWINGSS

DETAILED DESCRIPTION

Figure 1:
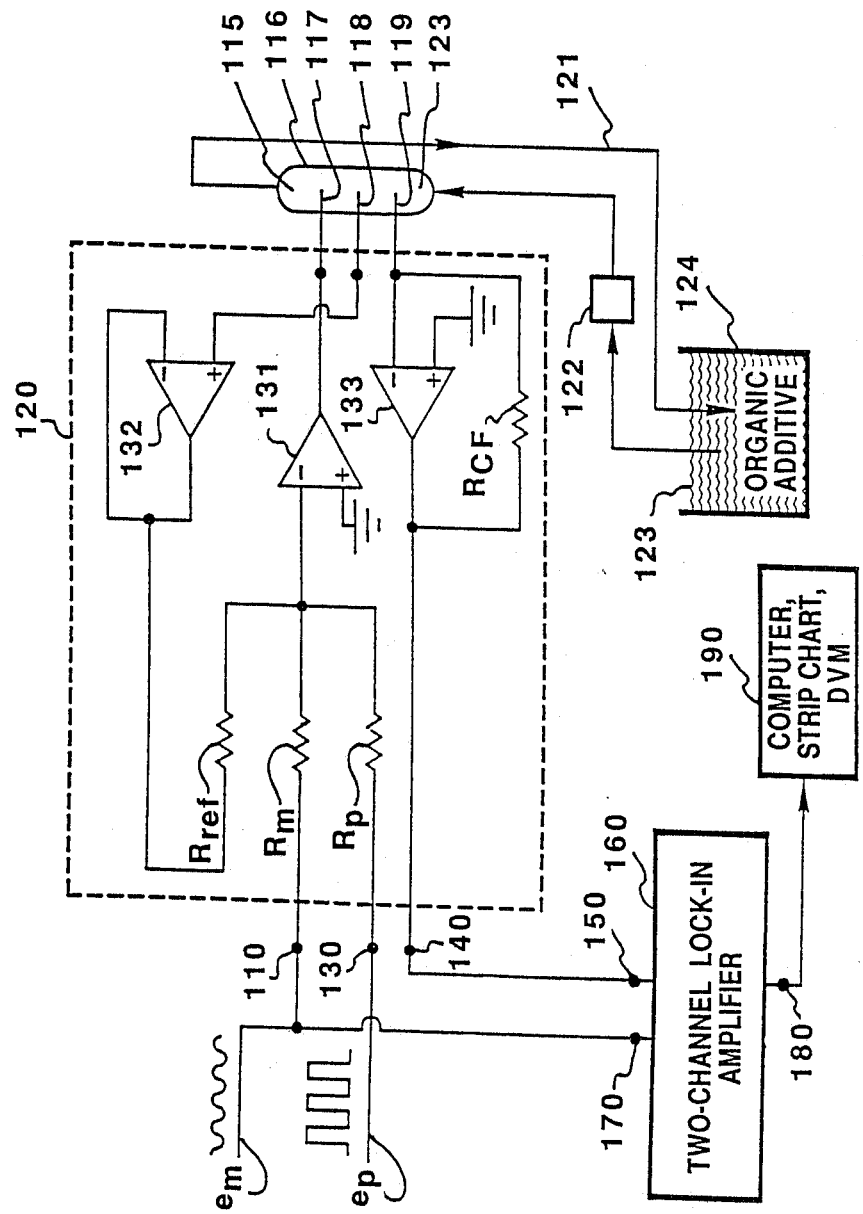
FIG. 1 is an electrical schematic of one embodiment illustrative of the invention.

Referring to FIG. 1, probe 115 comprises a cylindrical enclosure 116 around three wire electrodes counter electrode 117, reference electrode 118, and working electrode 119. Enclosure 116 may be, for example, a glass tube. Counter electrode 117 and working electrode 119 are selected to be any metal more noble than reference electrode 118. Reference electrode 118 is selected to match the application. In a copper plating application for example, electrodes 117 and 119 may be platinum or gold, and reference electrode 118 may be copper. In a lead plating application, reference electrode 118 would be lead. The electrodes may alternatively comprise a structure having an exterior surface matched to the plating application and an interior composed of, for example, a less expensive material.

In one embodiment, enclosure 116 had an inside diameter of approximately 20 mm, and each electrode extended longitudinally 50 mm into enclosure 116 with an inter-electrode spacing of about 10 mm.

The ends of enclosure 116 may be connected to plating bath 124 through pipes 121. Pump 122 causes electrolytic liquid 123 from bath 124 to flow through probe 115 and contact electrodes 116, 117 and 118. Alternatively, probe 115 may comprise a hand-held wand which may be dunked into plating bath 124.

Liquid 123 in bath 124 may be, for example, an acid-copper formulation containing approximately 28 oz/gal copper sulfate and 7 ox/gal sulfuric acid. A commercial additive marketed by Oxy Metal Incorporated of Warren, Michigan as "UBAC No. 1 Brightener" may be used at various concentrations ranging from 0.01 to 0.2 volume percent. This additive has several organic ingredients; one of these ingredients is discussed in U.S. Pat. No. 2,882,209.

A modulated voltage $E_M$ is applied to input 110 of potentiostat 120. Voltage $E_M$ may be, for example, sinusoidal at a frequency between about 100 to 10,000 Hz, and have an amplitude between about 5 to 50 mv. The theory underlying the selection of the frequency and amplitude of voltage $E_M$ will be discussed in greater detail below.

Potentiostat 120 may be a standard adder potentiostat such as the model 173 made by Princeton Applied Research, Princeton, New Jersey. The theory and operation of such potentiostats is further described in the work by A. J. Bard and L. R. Faulkner entitled "Electrochemical Methods, Fundamentals and Applications", Wiley, New York, 1980, pages 563-567. The theory and operation of potentiostats is well known in the electroplating art.

A DC bias voltage $E_P$ is applied to input 130 of potentiostat 120. Voltage $E_P$ may be a straight DC bias of, for example, between 0 to 500 mv. Optionally, when necessary for cleaning working electrode 119, voltage $E_P$ may be stepped between the initial bias level and about 1000 mv at a frequency between about 0.1 to 100 Hz.

Output 140 of potentiostat 120 is connected to input 150 of two-channel lock-in amplifier 160. Amplifier 160 may be, for example, the model 5206 made by Princeton Applied Research. Input 170 of amplifier 160 is connected to voltage $E_M$. Output 180 of amplifier 160 is connected to utilization device 190. Utilization device 190 may be, for example, a computer, a chart recorder, a digital volt meter or other device for realtime process control.

Counter electrode 117 is connected to the output of summing amplifier 131. Modulation voltage $E_M$ is applied to the summing point (inverting input) of amplifier 131 via resistor $R_M$. DC bias voltage $E_P$ is also applied to the summing point of amplifier 131 via resistor $R_P$.

Reference electrode 118 is connected to the noninverting input of voltage following amplifier 132. The output of amplifier 132 is applied to the inverting input (summing point) of amplifier 131 via resistor $R_{REF}$.

Working electrode 119 is connected to the inverting input of current following amplifier 133. Amplifier 133 includes feedback resistor $R_{CF}$ connected between its input and output. The output of amplifier 133 is connected to output 140 of potentiostat 120 and input 150 of lock-in amplifier 160.

In operation, DC bias voltage $E_P$ at counter electrode 117 causes metal ions within electrolytic liquid 123 in enclosure 116 to flow toward working electrode 119. The metal ions adsorb (reversibly) on working electrode 119 as a fraction of a monolayer if DC bias voltage $E_P$ is within the underpotential deposition (UPD) range for the metal being plated. The range for copper being deposited on copper is about 0 to 500 mv.

Organic additives in liquid 123 are also attracted to working electrode 119. The additives block active sites on working electrode 119 and thereby increase the resistance to the charge transfer required for UPD.

As the surfactant adsorbs and UPD occurs on working electrode 119, the impedance of the working electrode changes. In order to maintain the bias necessary for UPD to continue, it is necessary to regulate the current output of amplifier 131. The output of amplifier 131 is responsive to the voltage seen by reference electrode 118, and the input voltages $E_M$ and $E_P$.

The theory of underpotential deposition of metals and the adsorption of organic plating additives is described in further detail in the article of J. C. Farmer entitled "Underpotential Deposition of Copper on Gold and the Effects of Thiourea Studied by AC Impedance", Journal of the Electrochemical Society 132, 11, 2640 (1985), herein incorporated by reference.

Current due to modulation voltage $E_M$ flows from counter electrode 117 through the increased resistance at working electrode 119. The increased resistance at working electrode 119 causes the phase of the voltage applied to the inverting input of amplifier 133 to lag with respect to the phase of the modulation voltage $E_M$.

In accordance with the invention, the phase of the output voltage from amplifier 133 is compared to the phase of the modulation voltage $E_M$ in lock-in amplifier 160. The result of the comparison, the phase difference, is output as a voltage signal from amplifier 160 to utilization device 190. This voltage correlates directly to the surfactant concentration adsorbed on working electrode 119.

Figure 2:
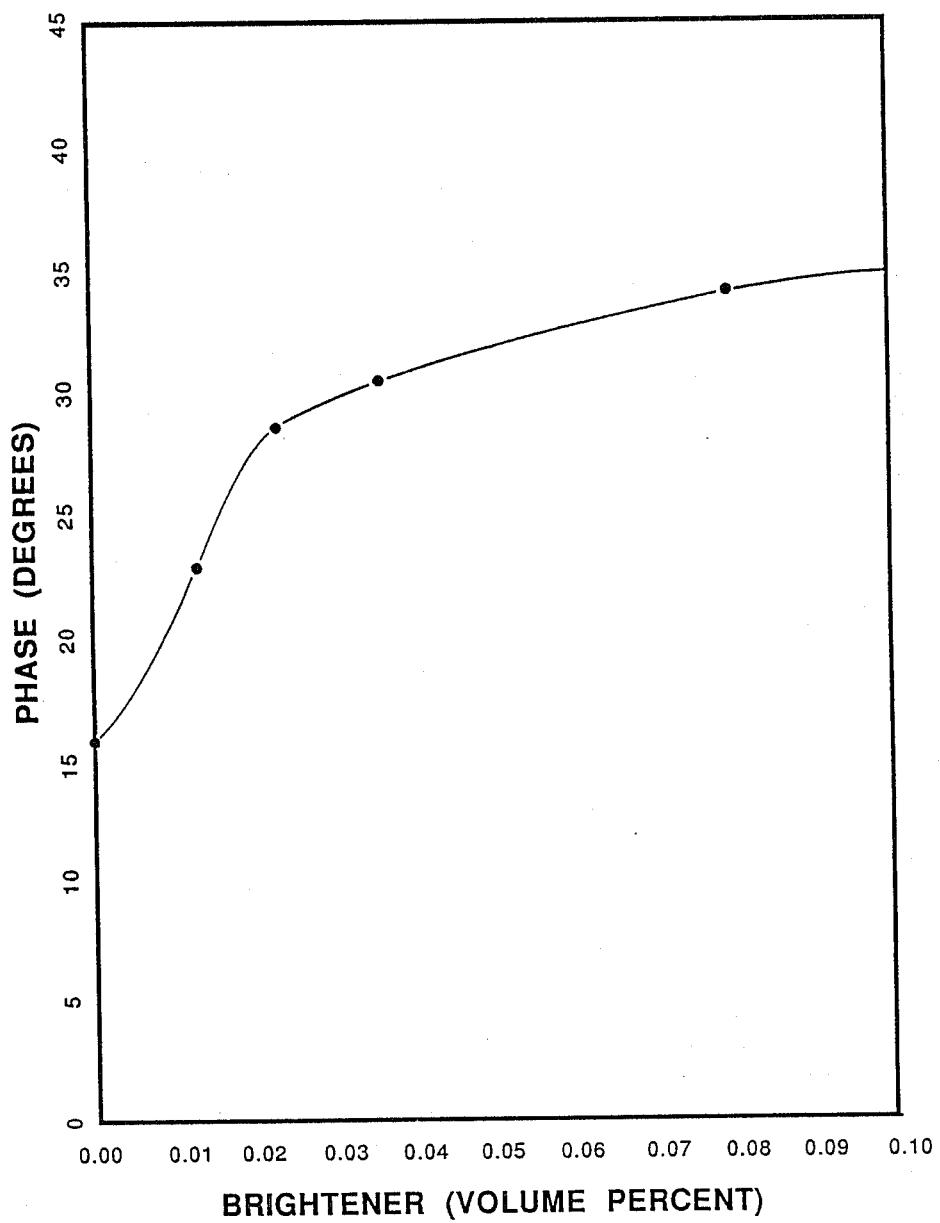
FIG. 2 is a graphical representation of the correlation between the surfactant concentration determined experimentally and the measured phase difference between the modulated voltage applied at the counter electrode and the current response at the working electrode.

FIG. 2 shows a typical calibration for a probe measurement according to the invention in the acid/copper formulation discussed above. Further details on the experimental calibration of the invention may be found in the document by J. C. Farmer, W. D. Bonivert and J. T. Hachman entitled "Tuned-Frequency Reversible Impedance Probe for the Measurement of Dilute Organic Additives in Electroplating Baths", Sandia Report SAND86-8227, which is incorporated herein by reference.

Certain organic plating additives, such as UBAC No. 1, will adsorb permanently to the surface of working electrode 119 if underpotential deposition continues uninterrupted. If the organic additive concentration were to fall, the change would not be detectable unless the surface of working electrode 119 were cleaned. Cleaning may be accomplished by stepping DC bias voltage $E_P$ periodically to a higher level where the organic is either oxidized or desorbed. The higher level may be, for example, about 1000 mv.

Turnign now to the theory underlying the selection of the frequency of voltage $E_M$, at potentials slightly anodic (positive) to that required for deposition of a bulk metal, a monolayer or less of that metal can be deposited on a more noble substrate, such as working electrode 119. This process, known as underpotential deposition (UPD), requires electron transfer at the surface of working electrode 119 and has an associated charge transfer resistance. Adsorbed organic plating additives block active sites on working electrode 119 and increase the charge transfer resistance.

The electrical impedance spectra of the noble metal working electrode during UPD is represented by equation 1:

$$Z = R_s + \left[ \frac{1 + j\omega R_p C_p}{R_p} - \frac{1}{p(1 + j\omega t)} \right]^{-1} \quad (1)$$

where Z is the complex impedance, $R_s$ is the electrolyte resistance, $R_p$ is resistance to charge transfer, $C_p$ is the double-layer capacitance at the working electrodeelectrolyte interface, p is a resistance which is almost equivalent to $R_p$, t is the low-frequency time constant, w is the angular modulation frequency, and j is the square root of $-1$.

The impedance converges to the electrolyte resistance at very high frequencies, and to a sum reflecting both the electrolyte resistance and the resistance to charge transfer during UPD at very low frequencies. It is important to note that very high frequency impedance measurements provide no information on additive adsorption. Low frequency measurements (sub-Hertz range) provide information on additive adsorption, but require computers applying Fast Fourier Transform techniques. Thus, measurements at low frequencies are inherently too slow for use as an online, realtime monitor.

The characteristic impedance also has a high-frequency time constant, $R_p C_p$, associated with it. This time constant and the electrolyte resistance determine one resonance frequency of working electrode 119, $\omega_{min}$, which can be calculated from equation 2:

$$\omega_{min} = (R_p C_p)^{-1} (1 + R_p/R_s)^{\frac{1}{2}} \quad (2)$$

The phase PHI passes through a minimum (maximum deviation from zero) at $\omega_{min}$. The magnitude of this phase minimum, $PHI_{min}$, can be calculated from equation 3:

$$\tan PHI_{min} = -\frac{R_p(1 + R_p/R_s)^{\frac{1}{2}}}{2(R_s + R_p)} \quad (3)$$

Measurement of the phase minimum allows determination of both $R_p$ and the additive concentration.

The phase minimum centered at $\omega_{min}$ covers a broad range of frequecies. Thus, measurements of phase at a single frequency near $\omega_{min}$ can be used to determine organic additive concentration, even though such measurements cannot be used to calculate $R_p$ exactly. For the embodiment of the device described in the above example of copper plating, we have determined that phase minimum measurements can occur at frequencies between about 100 to 10,000 Hz.

The phase angle between Y' and Y", the real and imaginary parts of the complex admittance, can be measured directly with a lock-in amplifier; this is identical to the phase difference between the modulation voltage $E_M$ and the response current at working electrode 118. This phase angle is equal in magnitude to the phase angle between Z' and Z", the real and imaginary parts of Z, but opposite in sign.

The amplitude of voltage $E_M$ is chosen to be only as large as necessary to provide the phase measurement of the invention, but not so large as to adversely affect the UPD of the material by the DC bias voltage. The frequency of voltage $E_M$ is $W_{min}$, as discussed above.

While the invention has been shown and described with reference to particular embodiments, it is to be understood that numerous changes may be made in form and details without departing from the spirit and scope of the invention. For example, the invention can be applied to measure capacitance of an electrode surface. Consequently, adsorbed species can also be measured in the absence of underpotential deposition. Therefore, the versions of the invention could be used to verify water purity. In the capacitance mode, functionalized electrodes could be used to detect components in biological samples. An electrode which would interact exclusively with the HTLV-III antibody, for example, could be used for screening blood supplies.

What is claimed is:

1. A method for measuring the concentration of a surfactant in a fluid electrolyte containing metal ions, comprising the steps of:
   surrounding a probe with the electrolyte, said probe comprising a reference electrode, a counter electrode, and a working electrode, said counter and working electrodes having outer surfaces more noble than the outer surfaces of said reference electrode, said electrodes being stationary in said probe relative to each other;
   applying a straight DC bias voltage at said counter electrode, the magnitude of said DC bias being selected to cause only underpotential deposition of metal from said electrolyte on said working electrode;
   adjusting the magnitude of said DC bias voltage responsive to the voltage at said reference electrode to maintain underpotential deposition of metal on said working electrode;
   applying an AC modulation voltage at the resonant frequency of said working electrode to said counter electrode;
   measuring the phase difference between the modulated voltage applied to said counter electrode and the current response to the modulated voltage at said working electrode; and
   correlating the phase difference to the concentration of surfactant in the electrolyte.

2. The method of claim 1 wherein said electrolyte is an electroplating solution and said surfactant is an organic additive in said solution.

3. The method of claim 2 further comprising the step of:
   cleansing the working electrode by stepping said DC bias voltage periodically to a voltage level selected to remove surfactants from said working electrode.

4. The method of claim 1 wherein the resonant frequency of said working electrode is the frequency of a phase minimum which occurs when the modulation is swept across a range of frequencies.

5. Apparatus for measuring the concentration of a surfactant in a fluid electrolyte containing metal ions, said apparatus comprising:
   a probe comprising a reference electrode, a counter electrode, and a working electrode, said counter and working electrodes having outer surfaces more noble than the outer surfaces of said reference electrode, said electrodes being stationary in said probe relative to each other;
   means for surrounding said probe with the electrolyte;
   means for applying a straight DC bias voltage at said counter electrode, the magnitude of said DC bias being selected to cause only underpotential deposition of metal from the electrolyte on said working electrode;
   means for adjusting the magnitude of said DC bias voltage responsive to the voltage at said reference electrode whereby underpotential deposition of metal is maintained on said working electrode;
   means for applying an AC modulation voltage at the resonant frequency of said working electrode to said counter electrode;
   means for measuring the phase difference between the modulated voltage applied to said counter electrode and the current response to the modulated voltage at said working electrode; and
   means for correlating the phase difference to the concentration of surfactant in the electrolyte.

6. Apparatus as in claim 5 wherein said electrolyte is an electroplating solution and said surfactant is an organic additive in said solution.

7. Apparatus as in claim 5 further comprising:
   means for cleansing the working electrode by stepping said DC bias voltage periodically to a level selected to remove surfactants from said working electrode.

8. Apparatus as in claim 5 wherein said probe comprises a glass tube, said electrodes consisting of wires extending into said tube.

9. Apparatus as in claim 8 wherein said counter and working electrodes are gold and said reference electrode is copper.

10. Apparatus as in claim 8 wherein said counter and working electrodes are gold and said reference electrode is lead.

11. Apparatus as in claim 8 wherein said counter and working electrodes are platinum and said reference electrode is copper.

12. Apparatus as in claim 8 wherein said counter and working electrodes are platinum and said reference electrode is lead.

* * * * *